(12) United States Patent
Liang et al.

(10) Patent No.: US 8,972,199 B2
(45) Date of Patent: Mar. 3, 2015

(54) PORTABLE EVALUATOR OF AMOUNT OF EXERCISE AND THE METHOD OF EVALUATING AMOUNT OF EXERCISE

(76) Inventors: Shien-Chi Liang, Taipei (TW); Yuan-Chin Chiang, Taipei (TW)

( * ) Notice: Subject to any disclaimer, the term of this patent is extended or adjusted under 35 U.S.C. 154(b) by 726 days.

(21) Appl. No.: 13/242,092

(22) Filed: Sep. 23, 2011

(65) Prior Publication Data

US 2012/0209532 A1    Aug. 16, 2012

(30) Foreign Application Priority Data

Feb. 15, 2011 (TW) .............................. 100104855 A (51) Int. Cl.
*G01N 33/48* (2006.01)
*A63B 71/00* (2006.01)
*G06F 19/00* (2011.01)

(52) U.S. Cl.
CPC .................................. *G06F 19/3481* (2013.01)
USPC .................................................. 702/19; 482/9

(58) Field of Classification Search
USPC ........................ 702/19, 33, 41, 127, 141–142, 702/149–153, 158, 160, 179, 188–189, 702/199; 482/8–9, 140–141; 700/91–92; 73/1.37–1.38, 1.75, 1.77, 488–493, 73/503.3, 504.02–504.03, 510–511, 73/514.01
See application file for complete search history.

(56) References Cited

U.S. PATENT DOCUMENTS

2012/0119911 A1* 5/2012 Jeon et al. .................. 340/573.1

* cited by examiner

*Primary Examiner* — Toan Le
(74) *Attorney, Agent, or Firm* — patenttm.us

(57) ABSTRACT

A portable evaluator of amount of exercise detects an acceleration and angular speed of the user. After using an exercise identifying procedure to identify the exercise type, the portable evaluator finds a corresponding strength formula to evaluate the amount of exercise done by the user. The result is displayed for reference. By detecting the acceleration and angular speed, the portable evaluator identifies exercise types that involve rotations. Different formulas are used for different kinds of exercise.

17 Claims, 9 Drawing Sheets

PORTABLE EVALUATOR OF AMOUNT OF EXERCISE AND THE METHOD OF EVALUATING AMOUNT OF EXERCISE

BACKGROUND OF THE INVENTION

1. Field of the Invention

The invention relates to a portable evaluator of amount of exercise and the method of evaluating amount of exercise. In particular, the invention relates to a portable evaluator of amount of exercise and the method of evaluating amount of exercise that can identify user's exercise type and use different formulas to calculate the amount of exercise thereof.

2. Description of Related Art

Due to changes in diet habit and lifestyle, obesity has become an important factor that affects human health nowadays. Countless cases of obesity eventually result in cardiovascular diseases. People are thus more conscious about weight control these days. According to most nutritionists, the best method to control weight is not restricted diet but regular exercise instead. In addition to having the habit of exercising daily or weekly, it is also important to have appropriate amount of exercise. However, the "appropriate" amount of exercise differs among people of different genders and builds. To evaluate whether a daily amount of exercise is too much or insufficient, an exerciser usually uses an evaluator of amount of exercise. The most common evaluator is the pedometer.

ROC Pat. No. TW 382450 discloses a pedometer that has a housing, a circuit board, a swinging element, and a triggering element. The circuit board has a switch. The triggering element is disposed on the swinging element. The step-counting principle is as the following. When the user walks one step, his or her body shakes up and down, which in turn swings the swinging element once. Every time the swinging element swings, the triggering element is driven to hit the switch of the circuit board. The switch is then turned on and off once to count the number of steps that the user has walked.

Besides, there is a tri-axis acceleration pedometer that uses tri-axis acceleration to count the number of steps. The device has an acceleration sensor for detecting the vertical vibrations (in the Z-axis, for example) caused by the user during a walk or run to obtain several peak values. A threshold peak value is also set in the tri-axis acceleration pedometer. Therefore, the detected peak values and the threshold peak values are compared to see how many peak values are greater than the threshold peak value, thereby determining the number of steps. In addition, the user's height can be entered as reference data for calculating the number of steps into a distance, thereby calculating a walking speed. The walking speed is plugged into a calorie consumption formula: 1.25×walking speed (C/Kg/h), to obtain the calorie consumed by the user.

However, the above-mentioned two pedometers only measure the vertical vibrations caused by walking or running. Exercises such as sit-up and push-up involve rotations that do not produce obvious vertical vibrations. Therefore, the above-mentioned two pedometers cannot evaluate the amount of such exercises. In other words, the above-mentioned two pedometers cannot be applied to users of all kinds of exercises.

SUMMARY OF THE INVENTION

In view of the foregoing, it is an objective of the invention to provide a portable evaluator of amount of exercise and the method of evaluating the amount of exercise.

To achieve the above-mentioned objective, the disclosed portable evaluator of amount of exercise includes:

an acceleration sensor for detecting and outputting an acceleration;

a gyroscope for detecting and outputting an angular speed;

a main controller, which is a control and operation center and built in with an exercise identifying procedure and an exercise strength evaluating procedure, the exercise strength evaluating procedure including a plurality of strength formulas for different exercises, links to the acceleration sensor and the gyroscope, establishes reference data after receiving the acceleration and angular speed output from the acceleration sensor and the gyroscope, executes the exercise identifying procedure to determine the strength formula for the exercise corresponding to the reference data, and computes and outputs an estimated amount of exercise from subsequently received reference data;

a display electrically connected to the main controller for displaying the estimated amount of exercise; and a power supplying unit for supplying operating power to the above-mentioned circuit.

Using the gyroscope and the acceleration sensor along with the exercise identifying procedure built in the main controller, the invention measures the angular speed and acceleration of the user to determine the current exercise type and to obtain the strength formula for the exercise, thereby calculating the exercise strength of the user. Therefore, not only can the invention measure acceleration caused by walking and running, it can also detect variations in the angular speed of the pitch as the user does push-ups and sit-ups. The invention uses such information to compute an amount of exercise.

Another objective of the invention is to provide a portable evaluator of amount of exercise that can more accurately determine the amount of exercise. The above-mentioned evaluator of amount of exercise further includes an extension module that has:

an appended acceleration sensor for detecting and outputting an acceleration;

an appended gyroscope for detecting and outputting an angular speed;

an appended controller electrically connected to the appended acceleration sensor and the appended gyroscope, receiving the acceleration and the angular speed to establish appended reference values and outputting the appended reference values;

a transmitting module electrically connected to the appended controller for outputting the appended reference values of the appended controller to the main controller; and an appended power supplying unit for providing operating power to the above-mentioned circuit.

For the above-mentioned extension module, the main controller further has a switch to switch the main controller to an extension sensing mode. After the switch switches to the extension sensing mode, the main controller then uses the appended reference values to establish the reference data.

By mounting the extension module onto a hand or head, the invention can better detect the acceleration and angular speed of the user through the appended acceleration sensor and gyroscope. This will further increase the accuracy of evaluation.

To achieve the above-mentioned objective, the disclosed method of evaluating amount of exercise includes the steps of:

receiving an acceleration and an angular speed to establish a reference database;

executing an exercise identifying procedure to identify the exercise of a user according to the reference database;

executing an exercise strength evaluating procedure that includes a plurality of strength formulas, uses a formula corresponding to the exercise determined by the exercise identifying procedure to convert the reference data into an estimated amount of exercise, and displaying the estimated amount of exercise.

The reference database includes acceleration and angular speed values. Not only can the invention detect accelerations due to walking and running, it can also detect variations in the angular speed caused by rotational motions of the user. With the exercise identifying procedure, the invention can identify what kind of exercise the user is currently doing. Moreover, the invention uses the corresponding formula to compute an estimated amount of exercise, thereby evaluating the amount of exercise of the user.

DETAILED DESCRIPTION OF THE PREFERRED EMBODIMENT

Figure 1:
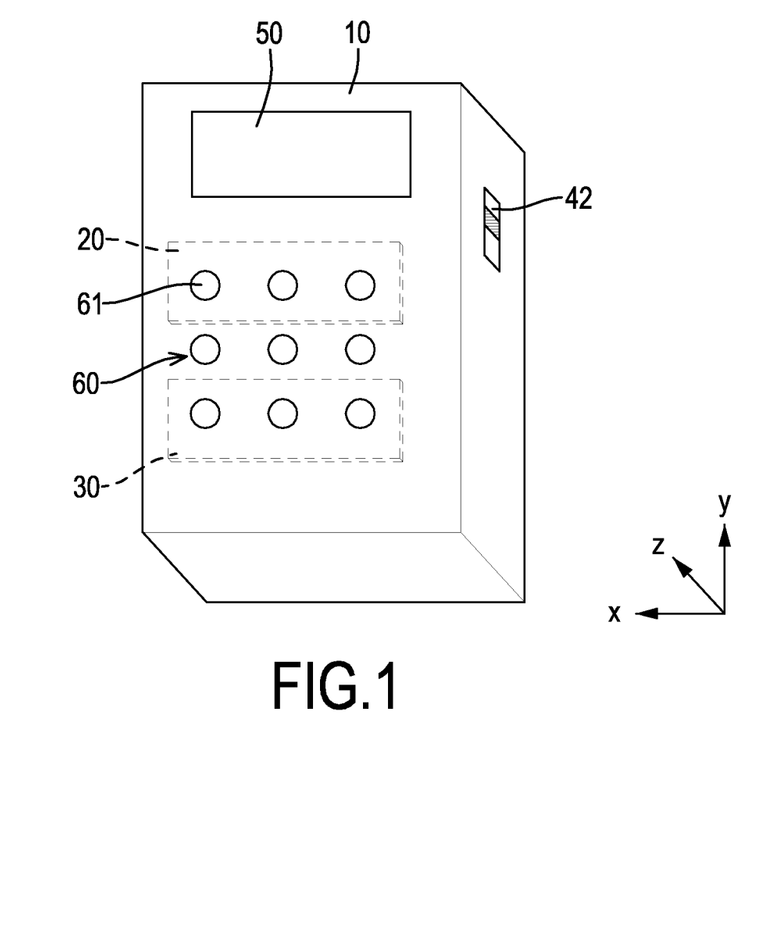
FIG. 1 is a perspective view of the invention.
Figure 2A:
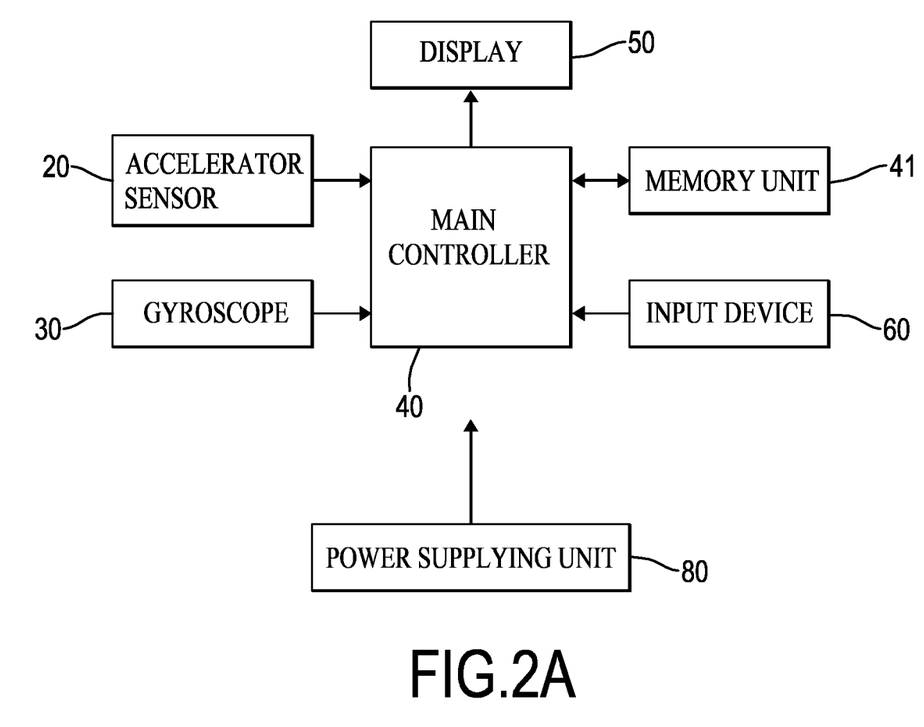
FIG. 2A is a circuit functional block diagram of the invention.

With reference to FIGS. 1 and 2A, a portable evaluator of amount of exercise includes a housing 10, an acceleration sensor 20, a gyroscope 30, a main controller 40, a display 50, an input device 60, and a power supplying unit 70.

The acceleration sensor 20 is disposed in the housing 10 to measure and output an acceleration. The gyroscope 30 is disposed in the housing 10 to measure and output an angular speed.

The main controller 40 is a control and operation center disposed in the housing 10. It is built in with an evaluating procedure that includes an exercise identifying procedure and an exercise strength evaluating procedure. The exercise strength evaluating procedure includes multiple strength formulas for several different exercises. The main controller 40 connects to the acceleration sensor 20 and the gyroscope 30. After receiving the acceleration and the angular speed from the acceleration sensor 20 and the gyroscope 30, the main controller 40 establishes reference data and executes the exercise identifying procedure to determine a strength formula of the identified exercise type corresponding to the reference data. The subsequently received reference data are used to calculate an estimated amount of exercise by using the determined strength formula. The calculated amount of exercise is then output. In this embodiment, the main controller 40 electrically connects to the acceleration sensor 20 and the gyroscope 30.

Figure 2B:
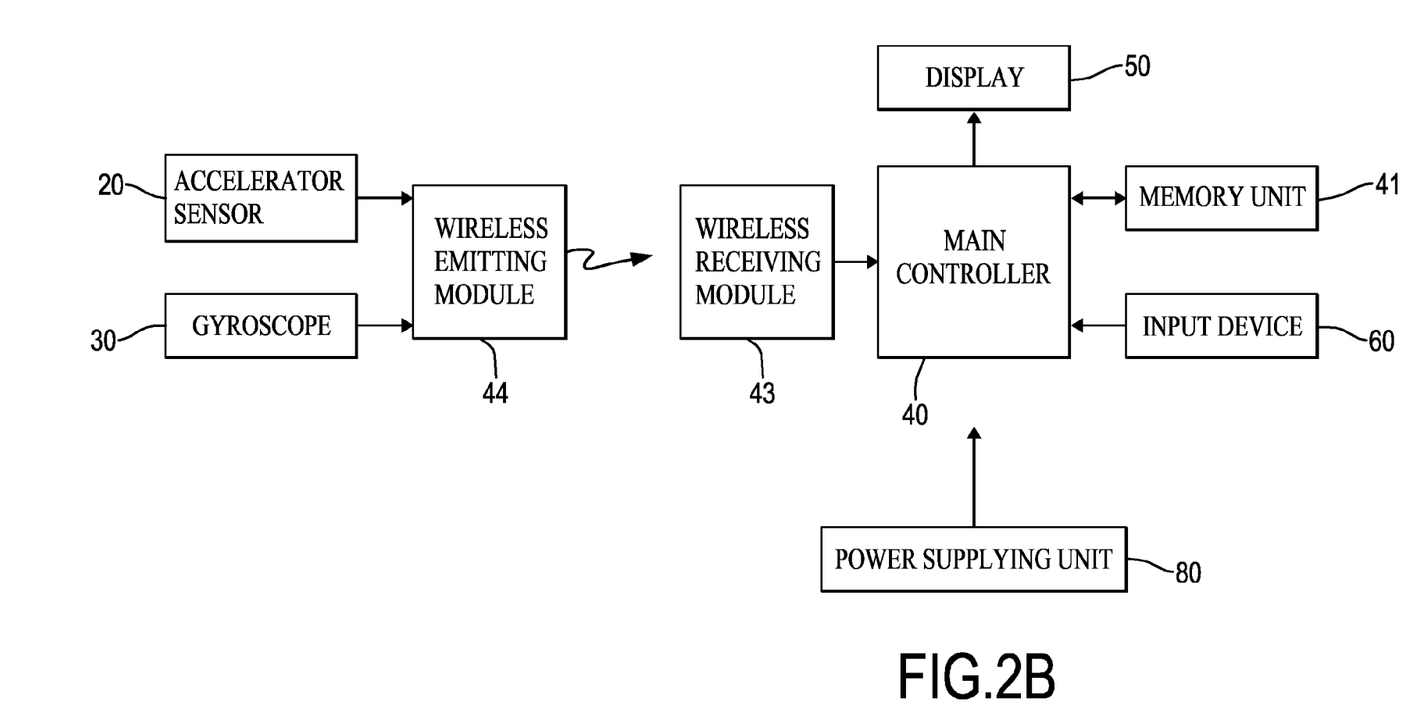
FIG. 2B is another circuit functional block diagram of the invention.

With reference to FIG. 2B showing another embodiment, the main controller 40 electrically connects to a wireless receiving module 43. The acceleration sensor 20 and the gyroscope 30 are connected to the main controller 40 via a wireless emitting module 44 corresponding to the wireless receiving module 43.

The main controller 40 further electrically connects to a memory unit 41 for storing the estimated amount of exercise. The memory unit 41 can be a volatile or non-volatile memory. The reference data include at least a Z-axis acceleration, an angular speed of pitching, and an angular speed of rolling. The X-, Y-, and Z-axes are shown in FIG. 1. The Z-axis is perpendicular to the acceleration sensor 20. The pitch is the angle with respect to the X-axis. The roll is the angle with respect to the Y-axis.

The display 50 is disposed on an outer surface of the housing 10 and electrically connected to the main controller 40. It is used to display the estimated amount of exercise from the main controller 40.

The input device 60 is disposed on the outer surface of the housing 10 and electrically connected to the main controller 40 for inputting user information. In this embodiment, the input device 60 is a button set, including a plurality of buttons 61. Alternatively, the input device 60 can be a microphone, a touch panel, or a communication port. The communication port is used to connect to an external input device, such as a USB port or UART port.

The power supplying unit 70 is disposed in the housing 10 for providing operating power for the above-mentioned circuits. It can be a non-rechargeable battery, rechargeable battery, or solar cell.

The above-mentioned acceleration sensor 20 and the gyroscope 30 can be integrated as a six-axis sensing chip.

Figure 3:
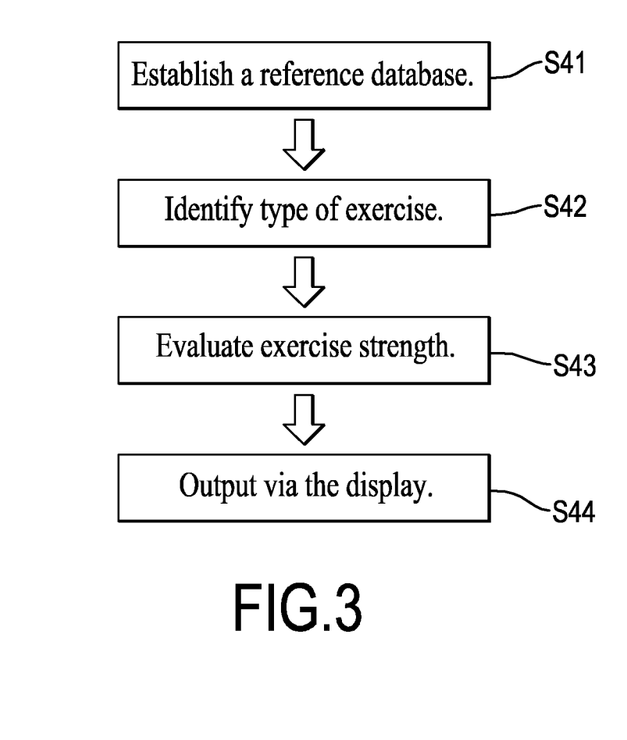
FIG. 3 is a flowchart of an evaluating procedure.

With reference to FIG. 3, the evaluating procedure includes the following steps.

Receive the acceleration and the angular speed values to establish a reference database S41. In this embodiment, the reference data built by the main controller 40 are used to establish the reference database.

Execute an exercise identifying procedure S42. In this embodiment, the distribution of the Z-axis acceleration in the reference database is used to identify that the exercise is push-up, sit-up or walking.

Execute a corresponding exercise strength evaluation S43. In this embodiment, there are different formulas for push-ups, sit-ups and walking. Based on the exercise determined by the exercise identifying procedure S42, a corresponding formula is taken to convert the reference data into an estimated amount of exercise. The display 50 then outputs the estimated amount of exercise in units of calories S44.

Figure 4:
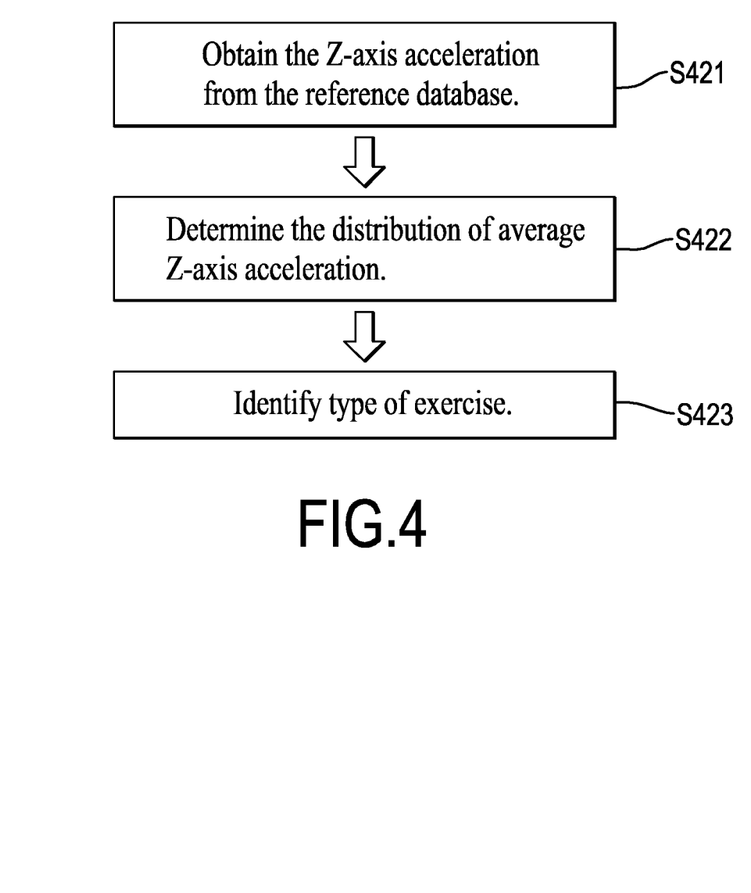
FIG. 4 is a flowchart of an exercise identifying procedure in FIG. 3.

With reference to FIG. 4, the exercise identifying procedure S42 further includes the following steps.

Obtain the Z-axis acceleration from the reference database S421.

Compute an average value of the Z-axis acceleration, and use the following criteria to determine the range it belongs to S422:

1. If the average value is between $-1.1$ g and $-0.9$ g, then the exercise is determined as push-up, wherein g is gravitational acceleration;

2. If the average value is between $0.6$ g and $1.1$ g, then the exercise is determined as sit-up; and 3. If the average value is between $-0.2$ g and $0.2$ g, then the exercise is determined as walking.

Use the range determined in the previous step S422 to determine the corresponding exercise S423.

How to determine the user's exercise type according to the invention has been described above. The following paragraphs describe how to evaluate the exercise strength for various exercise types according to the invention.

Figure 5:
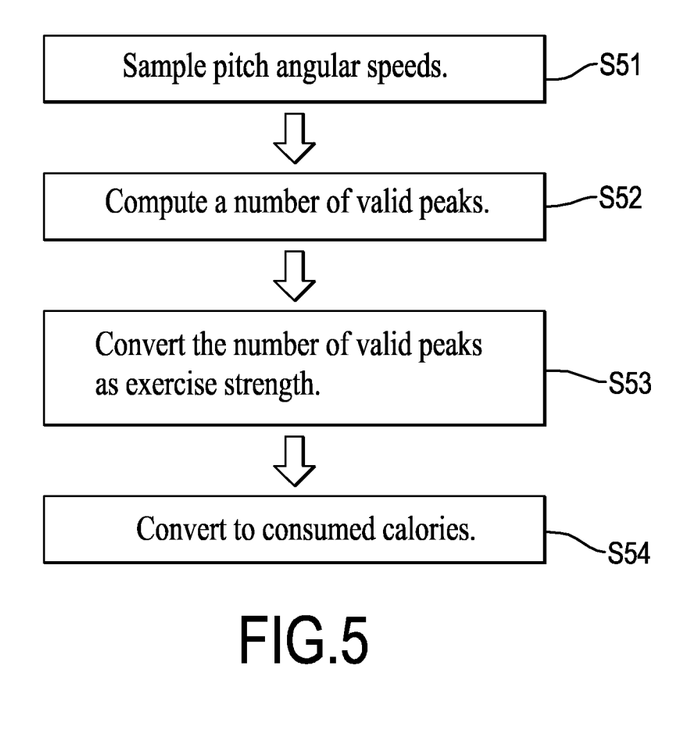
FIG. 5 is a flowchart for one exercise strength formula in the exercise strength evaluation.

With reference to FIG. 5, when the exercise currently performed by the user is push-up or sit-up, the formulas for computing the exercise strength in these two cases involve the following steps.

Obtain the angular speed of the pitch from the reference data S51, and perform sampling in the angular speed.

Compute the number of valid peaks of the pitch angular speed per minute S52. Build in a peak threshold and an effective peak value. Set the sample value that is smaller than the peak threshold in the above-mentioned sampling as zero, i.e. excluding the sample values smaller than the peak threshold. Determine the number of peaks in the sampling per minute as the number of valid peaks. When the sampling time is less than one minute, the number of valid peaks is computed in proportion. In this embodiment, if the (n+1)-th sample value is smaller than the n-th sample value and the n-th sample value is greater than the (n−1)-th sample value, the n-th sample value is considered as a peak.

Convert the number of valid peaks into consumed calories S53. From experimental observations, it is learned that the pitch angular speed generates three peaks in each standard push-up and that the pitch angular speed generates two peaks in each standard sit-up. Therefore, in this embodiment a first standard value per minute is set for the exercise strength formula associated with push-ups. The first standard value per minute means the standard number of push-ups in each minute. The number of the valid peaks per minute is then divided by three, and then divided by the first standard value per minute, thereby obtaining an exercise strength value. This exercise strength value means the ratio between the exercise strength of the user per minute and the first standard value per minute. A second standard value per minute is also set for the formula associated with sit-ups. The number of valid peaks per minute is divided by two, and then divided by the second standard value per minute, thereby also obtaining an exercise strength value.

Convert the exercise strength value into consumed calories S54. In this embodiment, the conversion formula is:

Consumed calories=exercise strength value×metabolism equivalent×exercise time(in units of minute)×body weight÷60.

For example, suppose the metabolism equivalent of push-ups and sit-ups is set as 8. The body weight is entered by the user via the input device 60. The consumed calories can thus be obtained and displayed by the display 50 for the user's reference.

Figure 6:
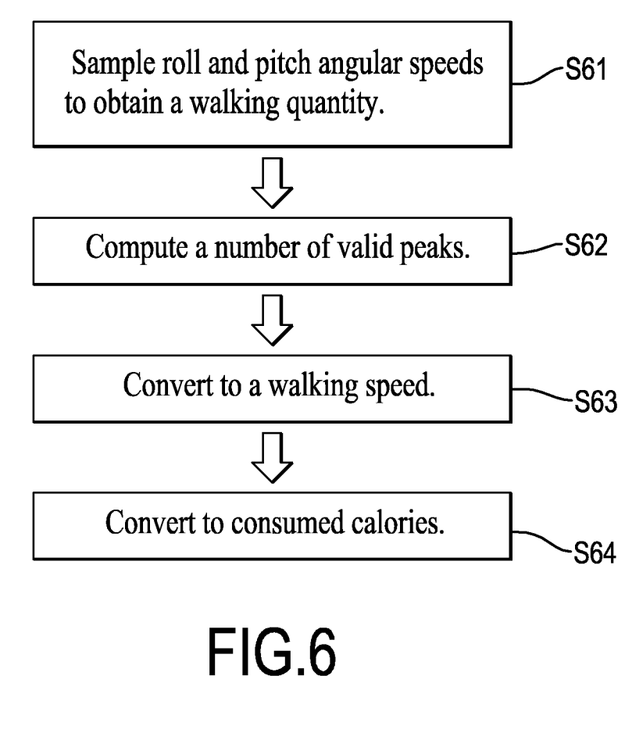
FIG. 6 is a flowchart for another exercise strength formula.

With reference to FIG. 6, in this example, the exercise is walking. The exercise strength in this case involves the following steps.

Obtain the angular speeds (r1, p1) of roll and pitch, and convert them into a walking quantity (w1) S61. In this embodiment, the walking quantity is equal to the square root of the sum of the squares of the two angular speeds, w1= $\sqrt{r1^2+p1^2}$. The walking quantity is then sampled.

Compute the number of valid peaks in the sampling of the walking quantity S62. First, set a peak threshold. Set the sample value of the walking quantity that is smaller than the peak threshold as zero, i.e. excluding the sample values smaller than the peak threshold. Determine the number of peaks in the sampling per minute as the number of the valid peaks. When the sampling time is less than one minute, the number of the valid peaks is computed in proportion. The number of valid peaks per minute represents the evaluated number of steps.

Convert the number of valid peaks per minute into a walking speed S63. The number of steps is converted into a walking speed based on the user's height. The user's height is entered by the user via the input device 60. The number of valid peaks per minute and the user's height are used as reference data for calculating the walking speed. For example, the user's height can correspond to a walking distance per step, and the walking speed can be obtained by multiplying the walking distance per step and the evaluated number of steps.

Convert the walking speed to consumed calories S64. In this embodiment, the calorie conversion formula is:

Consumed calories=((total metabolism equivalent−1)×3.5×body weight÷200)×exercise time;

wherein total metabolism equivalent=total oxygen consumption÷3.5 and total oxygen consumption=3.5+0.1×walking speed.

The walking speed and the body weight are converted into consumed calories based on the foregoing formula. The body weight is entered by the user via the input device 60.

Figure 7A:
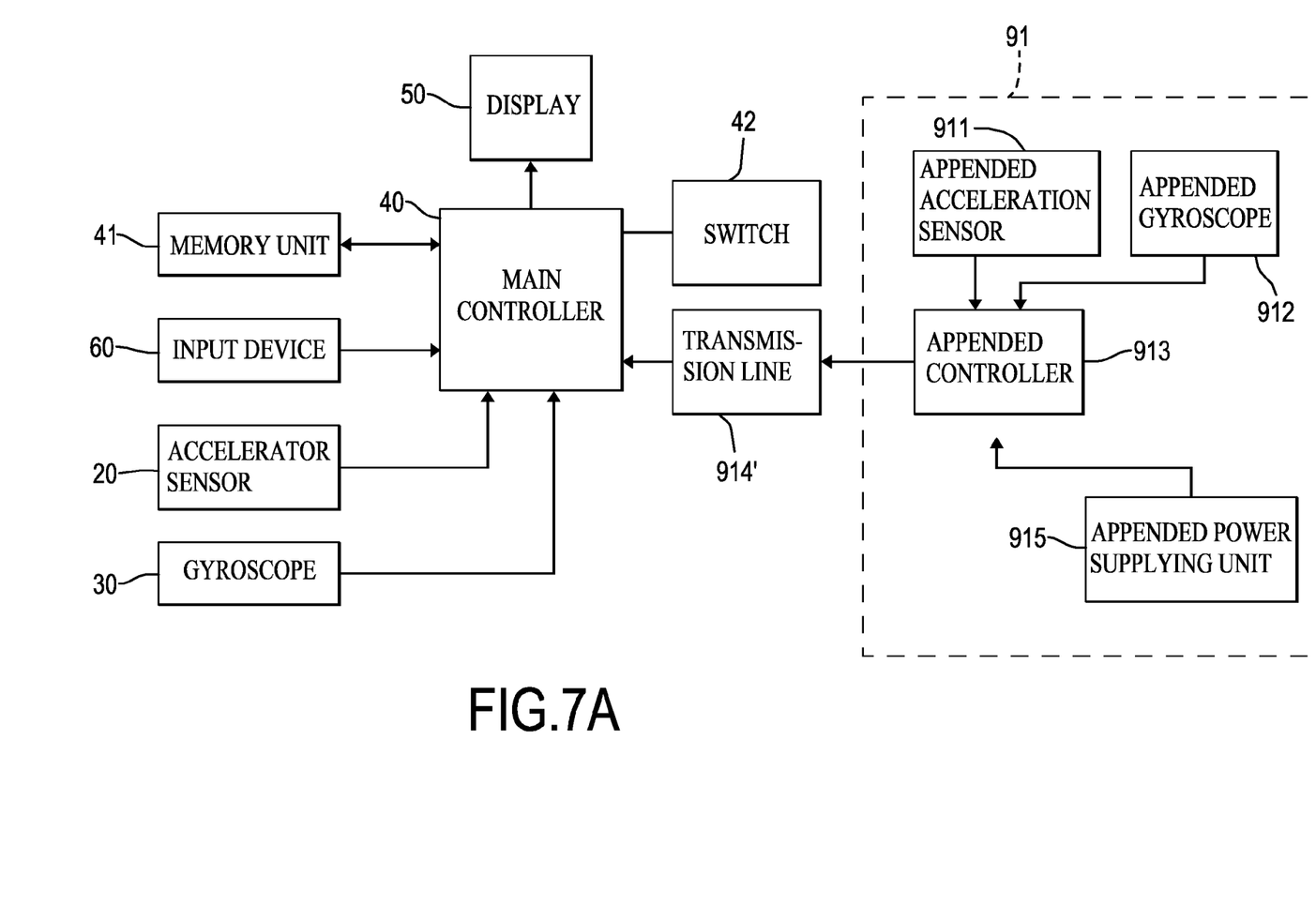
FIG. 7A is a functional block diagram for another embodiment of the invention.

With reference to FIG. 7A, an extension module 91 is added. The extension module 91 includes an appended acceleration sensor 911, an appended gyroscope 912, an appended controller 913, a transmission module and an appended power supplying unit 915.

The appended acceleration sensor 911 detects and outputs an acceleration. The appended gyroscope 912 detects and outputs an angular speed. The appended controller 913 electrically connects to the appended acceleration sensor 911 and the appended gyroscope 912 and receives the acceleration and the angular speed to establish and output appended reference values. The transmission module outputs the appended reference values to the main controller 40. The appended power supplying unit 915 supplies operating power to the above-mentioned circuits.

Figure 7B:
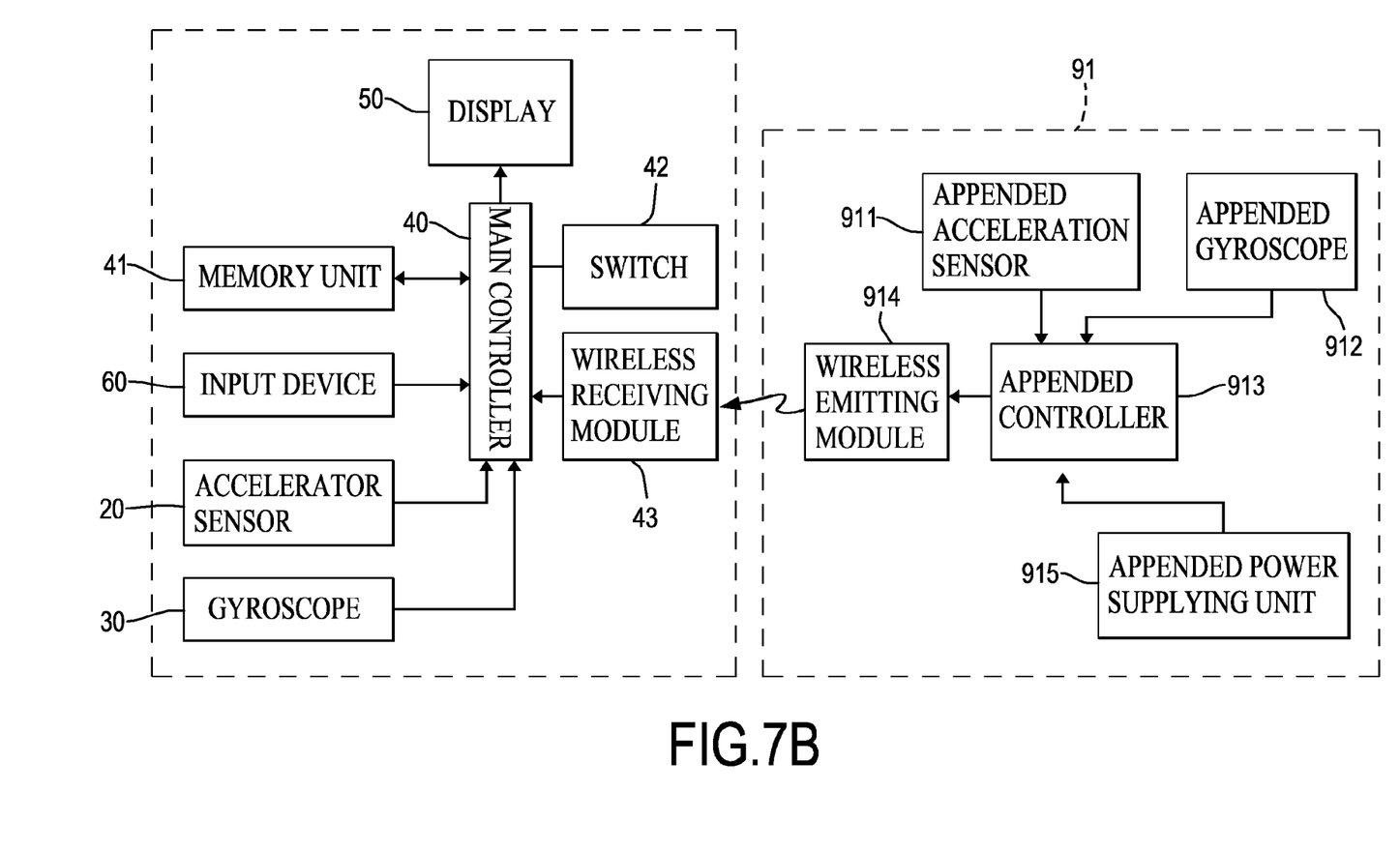
FIG. 7B is a functional block diagram for yet another embodiment of the invention.

The transmission module in this embodiment is a transmission line 914' electrically connected to the main controller 40. Alternatively, as shown in FIG. 7B, the transmission module is a wireless emitting module 914. The main controller 40 further connects to a wireless receiving module 43 that communicates with the wireless emitting module 914.

Moreover, the main controller 40 is provided with a switch 42 and built in with an extension sensing mode.

Figure 8:
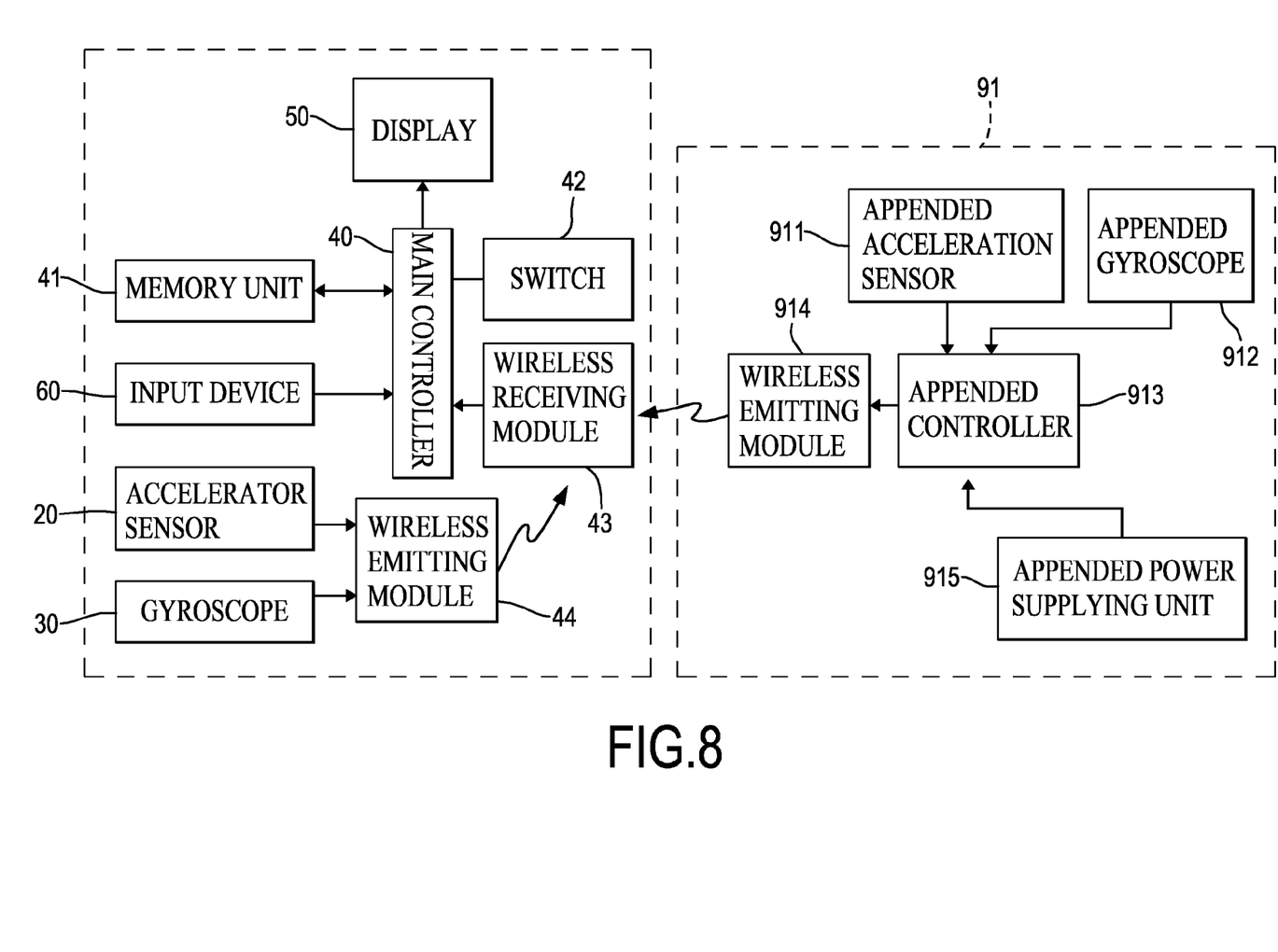
FIG. 8 is a functional block diagram for yet another embodiment of the invention.
Figure 9:
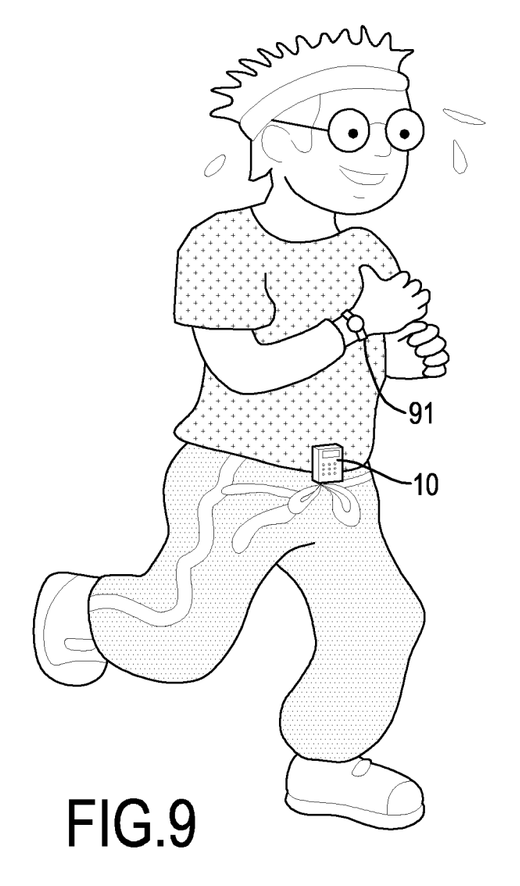
FIG. 9 is a schematic view of the invention in use.

With reference to FIG. 8, another embodiment modified based on FIG. 2B comprises an extension module 91. The extension module 91 includes an appended acceleration sensor 911 for detecting and outputting an acceleration; an appended gyroscope 912 for detecting and outputting an angular speed; an appended controller 913 electrically connecting to the appended acceleration sensor 911 and the appended gyroscope 912 and receiving the acceleration and the angular speed to establish and output appended reference values; a transmission module for outputting the appended reference values to the main controller 40; and an appended power supplying unit 915 for supplying operating power of the above-mentioned circuits.

The transmission module in this embodiment is a wireless emitting module 914 electrically connected to the wireless receiving module 43 of the main controller 40. Alternatively, the transmission module can be a transmission line 914', as in FIG. 7A.

The main controller 40 is further provided with a switch 42 and built in with an extension sensing mode. When using the switch 42 to switch the main controller 40 to the extension sensing mode, the main controller 40 uses the appended reference values to establish the reference data. In this case, the extension module 91 can be provided with a wearing element (e.g., a watch, belt, etc) to be worn around the wrist or waist that has more significant motion during the exercise. The appended acceleration sensor 911 and the appended gyroscope 912 can measure more accurate values for the main controller 40 to provide precise estimates.

In summary, the invention utilizes the gyroscope and the acceleration sensor along with the exercise identifying procedure and the exercise strength evaluating procedure to first determine the kind of exercise and then evaluate the exercise strength in a corresponding way. Therefore, not only can the invention detect the acceleration caused by walking and running, it can also detect variations in the pitch angular speed caused by push-ups and sit-ups. The present invention then determines the corresponding exercise strength to accurately evaluate the amount of exercise of the user.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A method of evaluating amount of exercise for a portable evaluator of amount of exercise, the method performed in a main controller of a portable evaluator and comprising:
   receiving accelerations and angular speeds to establish a reference database including Z-axis accelerations, pitch angular speeds, and roll angular speeds;
   executing an exercise identifying procedure to determine a type of exercise performed by a user based on the reference database, wherein
      the exercise identifying procedure uses a distribution of the Z-axis accelerations in the reference database to determine whether the exercise is push-up, sit-up or walking;
      the exercise identifying procedure comprises:
         obtaining the Z-axis accelerations in the reference database;
         calculating an average value of the Z-axis accelerations; and
         determining the exercise by checking which of the following ranges the average value falls into:
            when the average value is between −1.1 g and −0.9 g, the exercise is push-up, wherein g is the gravitational acceleration;
            when the average value is between 0.6 g and 1.1 g, the exercise is sit-up; and
            when the average value is between −0.2 g and 0.2 g, the exercise is walking; and
   executing an exercise strength evaluating procedure that includes a plurality of strength formulas for push-up, sit-up and walking, uses a formula corresponding to the type of exercise determined in the exercise identifying procedure to convert reference data in the reference database into an estimated amount of exercise, and displays the estimated amount of exercise.

2. The method as claimed in claim 1, wherein when the exercise is determined as push-up, the strength formula for the push-up comprises:
   obtaining pitch angular speeds from the reference database, and sampling the pitch angular speeds to obtain multiple sample values;
   computing a number of valid peaks per minute associated with the pitch angular speeds by
      setting a peak threshold and a number of valid peaks;
      setting sample values less than the peak threshold as zero; and
      determining a number of peaks in the sampling per minute as the number of the valid peaks per minute;
   converting the number of the valid peaks into consumed calories by
      setting a reference value per minute that represents a basis number of push-ups per minute;
      dividing the number of the valid peaks per minute by 3 to obtain a result; and
      dividing the result by the reference value per minute to obtain an exercise strength value; and
   converting the exercise strength value into consumed calories using a formula: consumed calories=exercise strength value×metabolism equivalent×exercise time (in units of minute)×body weight÷60.

3. The method as claimed in claim 1, wherein when the type of exercise is determined as sit-up, the strength formula for sit-up comprises:
   obtaining pitch angular speeds from the reference database and sampling the pitch angular speeds to obtain multiple sample values;
   computing a number of valid peaks per minute associated with the pitch angular speed by
      setting a peak threshold and a number of valid peaks;
      setting sample values less than the peak threshold as zero; and
      determining a number of peaks in the sampling per minute as the number of valid peaks per minute;
   converting the number of valid peaks into consumed calories by
      setting a reference value per minute that represents a basis number of sit-ups per minute;
      dividing the number of valid peaks per minute by 2 to obtain a result; and
      dividing the result by the reference value per minute to obtain an exercise strength value; and
   converting the exercise strength value into consumed calories using the formula: consumed calories=exercise strength value×metabolism equivalent×exercise time (in units of minute)×body weight÷60.

4. The method as claimed in claim 3, wherein when the type of exercise is determined as walking, the strength formula for walking comprises:
   obtaining pitch and roll angular speeds and converting the pitch and roll angular speeds into a walking quantity, the walking quantity being a square root of a sum of squares of the pitch and roll angular speeds, and sampling the walking quantity to obtain multiple sample values;
   computing a number of valid peaks per minute associated with the sample values by
      setting a peak threshold;
      setting sample values less than the peak threshold as zero; and
      determining a number of peaks in the sampling per minute as the number of valid peaks per minute to represent an estimated number of steps;

converting the number of the valid peaks per minute into a walking speed by referring to the estimated number of steps and a user's height; and converting the walking speed into consumed calories using a formula: consumed calories=((total metabolism equivalent−1)×3.5×body weight÷200)×exercise time, wherein total metabolism equivalent=total oxygen consumption÷3.5, and total oxygen consumption=3.5+0.1× the walking speed.

5. The method as claimed in claim 1, wherein when the type of exercise is determined as walking, the strength formula for walking comprises:

obtaining pitch and roll angular speeds and converting the pitch and roll angular speeds into a walking quantity, the walking quantity being the square root of a sum of the squares of the pitch and roll angular speeds, and sampling the walking quantity to obtain multiple sample values;

computing a number of valid peaks per minute associated with the sample values by setting a peak threshold;

setting sample values less than the peak threshold as zero; and determining a number of peaks in the sampling per minute as the number of valid peaks per minute to represent an estimated number of steps;

converting the number of the valid peaks per minute into a walking speed by referring to the estimated number of steps and a user's height; and converting the walking speed into consumed calories by referring to the walking speed and the user's weight to the consumed calories.

6. A portable evaluator performing the method as claimed in claim 1 and comprising:

an acceleration sensor for detecting and outputting an acceleration;

a gyroscope for detecting and outputting an angular speed;

a main controller connected to the acceleration sensor and the gyroscope, receiving the acceleration and the angular speed of current exercise from the acceleration sensor and the gyroscope, and executing the exercise identifying procedure and the exercise strength evaluating procedure to obtain the estimated amount of exercise;

a display electrically connected to the main controller for displaying the estimated amount of exercise output by the main controller; and a power supplying unit for supplying operating power to the above-mentioned circuits.

7. The portable evaluator as claimed in claim 6 further comprising:

an input device;

the main controller further comprising a memory unit, the input device electrically connected to the main controller for entering user information, wherein the memory unit stores the data for the main controller, thereby recording the estimated amount of exercise of the user.

8. The portable evaluator as claimed in claim 7, wherein the main controller electrically connects to a wireless receiving module, and the acceleration sensor and the gyroscope communicate with the main controller via a wireless emitting module and the wireless receiving module.

9. The portable evaluator as claimed in claim 8 further comprising an extension module comprising:

an appended acceleration sensor for detecting and outputting an acceleration;

an appended gyroscope for detecting and outputting an angular speed;

an appended controller electrically connected to the appended acceleration sensor and the appended gyroscope for receiving the acceleration and the angular speed and generating appended reference values;

a transmission module for outputting the appended reference values of the appended controller to the main controller; and an appended power supplying unit for supplying operating power;

wherein the main controller is provided with a switch and built in with an extension sensing mode, and when the main controller is switched by the switch into the extension sensing mode, the appended reference values of the extension module are used to establish the reference database.

10. The portable evaluator as claimed in claim 9, wherein the transmission module is a wireless emitting module corresponding to the wireless receiving module of the main controller.

11. The portable evaluator as claimed in claim 9, wherein the transmission module is a transmission line electrically connected to the main controller.

12. The portable evaluator as claimed in claim 7 further comprising a housing, wherein the acceleration sensor, the gyroscope, the main controller, and the power supplying unit are mounted in the housing, and the display and the input device are mounted on an outer surface of the housing.

13. The portable evaluator of amount of exercise as claimed in claim 7, wherein the acceleration sensor and the gyroscope are integrated as a six-axis sensing chip.

14. The portable evaluator of amount of exercise as claimed in claim 6 further comprising an extension module comprising:

an appended acceleration sensor for detecting and outputting an acceleration;

an appended gyroscope for detecting and outputting an angular speed;

an appended controller electrically connected to the appended acceleration sensor and the appended gyroscope for receiving the acceleration and the angular speed and generating appended reference values;

a transmission module for outputting the appended reference values of the appended controller to the main controller; and an appended power supplying unit for supplying operating power;

wherein the main controller is provided with a switch and built in with an extension sensing mode, and when the main controller is switched by the switch into the extension sensing mode, the appended reference values of the extension module are used to establish the reference database.

15. The portable evaluator as claimed in claim 14, wherein the transmission module is a wireless emitting module and the main controller is provided with a corresponding wireless receiving module.

16. The portable evaluator of amount of exercise as claimed in claim 14, wherein the transmission module is a transmission line electrically connected to the main controller.

17. The portable evaluator of amount of exercise as claimed in claim 6, wherein the acceleration sensor and the gyroscope are integrated as a six-axis sensing chip.

* * * * *